United States Patent

Westenskow et al.

[11] 4,127,121
[45] Nov. 28, 1978

[54] OXYGEN AND ANESTHESIA DELIVERY AND MONITORING DEVICE

[75] Inventors: Dwayne R. Westenskow; Curtis C. Johnson, both of Salt Lake City, Utah

[73] Assignee: University of Utah, Salt Lake City, Utah

[21] Appl. No.: 724,194

[22] Filed: Sep. 17, 1976

[51] Int. Cl.² .................................... A61M 16/00
[52] U.S. Cl. .......................... 128/142 R; 128/209; 128/188
[58] Field of Search ............ 128/142 R, 142.2, 142.3, 128/145.5, 145.6, 145.8, 188, 209, 210, DIG. 17, 2.08, 191 R, 191 A; 137/93

[56] References Cited

U.S. PATENT DOCUMENTS

| | | | |
|---|---|---|---|
| 1,759,996 | 5/1930 | Parker | 137/93 |
| 2,754,819 | 7/1956 | Kirschbaum | 128/188 |
| 3,251,361 | 5/1966 | Rusz | 128/188 |
| 3,465,753 | 9/1969 | Levy et al. | 128/188 |
| 3,593,735 | 7/1971 | Reiher | 128/142 R X |

*Primary Examiner*—Henry J. Recla
*Attorney, Agent, or Firm*—Criddle, Thorpe and Western

[57] ABSTRACT

A device for continuously monitoring oxygen consumption and anesthesia gas uptake of surgical patients, having servo-controlled replenishment mechanisms to automatically maintain preset levels of oxygen and anesthesia gas for inhalation. A closed, recirculating delivery circuit is utilized to adminster an appropriate volume of oxygen and anesthesia gas to a surgical patient. An oxygen sensor monitors decreases in oxygen concentration within the recirculatory system and triggers restoration to the preset concentration by means of feedback comparator circuitry. With the oxygen held at the desired level, any volume changes in the system are caused by uptake of anesthesia gas, which is monitored by detecting variations in the expansion of a respirator bellows. The desired amount of anesthesia gas is preset and maintained by a potentiometric monitoring device which produces a voltage proportional to the peak expansion of the bellows. Variations from the preset level of anesthesia gas drive a servo-mechanism for replenishing the anesthesia gas to the preset value. Data relating to oxygen consumption and anesthesia gas uptake are displayed by means of conventional instrumentation.

7 Claims, 1 Drawing Figure

OXYGEN AND ANESTHESIA DELIVERY AND MONITORING DEVICE

The invention described herein was made in the course of work under a grant from the National Institute of Health, Department of Health, Education, and Welfare.

BACKGROUND OF THE INVENTION

The concurrent monitoring of oxygen consumption and anesthesia uptake during surgery provides significant information which can assist the attending physician in intraoperative and post operative patient care. In particular, whole body oxygen consumption ($VO_2$) can indicate physiological changes which may prove fatal if not properly treated. Such conditions include respiratory failure, injury and many pathophysiological disorders resulting from inadequate cellular metabolism. $VO_2$ in critically ill patients serves as a measure of cardiovascular function and tissue perfusion, as well as a parameter for the calculation of cardiac output by the Fick principle. Furthermore, oxygen transfer and transport requirements during surgery can be monitored in view of the dependence of such functions on the rate of $VO_2$ by the tissues.

Concurrently with oxygen consumption measurements, the rate of uptake of anesthesia may require monitoring, particularly in a closed system or rebreathing administration apparatus. In addition to enabling maintenance of appropriate tissue saturation, a knowledge of actual anesthesia gas uptake may provide useful information as a research tool in evaluating anesthetics and various forms of instrumentation.

Numerous methods for measuring $VO_2$ have been used, all but a few of which fit into one of two groups. The most often used and simplest method is the closed circuit method which uses a spirometer filled with oxygen from which the patient breathes. The reduction in volume gives direct measurement of $VO_2$. The second method, the open circuit method, calculates $VO_2$ by subtracting the product of the expired percent oxygen and expired volume from the product of the inspired percent and volume.

The need for monitoring $VO_2$ of critically-ill and surgical patients who often require artificial ventilation with oxygen-enriched air is not filled by either of these methods. The closed circuit spirometer method does not provide a continuous record and is very susceptible to leaks or changes in lung volume, thereby creating a non-steady state condition with regard to nitrogen or the concurrently applied nitrous oxide. The open circuit method does provide a continuous record but its accuracy is decreased due to variations in oxygen concentration supplied to the patient. Since the oxygen concentration may change during inspiration and from breath to breath, flow weighted averages of both inspired and expired air are needed. During anesthesia, the open circuit technique requires the measurement of both inspired and expired volumes since the simple calculations of these volumes become inaccurate when dealing with such gases as nitrous oxide. Equipment for measuring these volumes is traditionally very bulky and requires a major revision of the conventional anesthesia delivery system. For these reasons, it is suggested that a closed system is preferred in monitoring oxygen consumption in surgical patients.

In cases where a closed anesthesia delivery system has been utilized, monitoring of oxygen and nitrous oxide has been a manual operation for the anesthesiologist. By observing a bellows system, anesthesia uptake is observed and resupply is effected by opening valves to release sufficient gas to bring the volume to an appropriate level. The oxygen concentration is maintained by similar means, relying perhaps on an oxygen sensor to indicate oxygen deficiency. The primary disadvantages of such a system include uncertainty as to actual consumption and uptake, inability to monitor rates of consumption and uptake, necessity to rely on subjective judgment of the anesthesiologist to make the appropriate replenishment, and the inconvenience and danger of requiring the constant attention of the anesthesiologist to monitor bellows and other instruments.

The principles of monitoring oxygen consumption of surgical patients has recently advanced into automated means when intravenous anesthetics are utilized. Such an instrument was disclosed at the IEEE 1975 Regional Six Conference and provides a closed circuit path with automated valving to feed an oxygen mixture into the circuit in accordance with a preset value. Upon exhalation of the oxygen mixture by the patient, the oxygen level is replenished to compensate for the oxygen deficiency indicated by an oxygen sensor in the circuit. A comparator circuit operates a servomotor to feed oxygen into the circuit until a null state is detected between the present reference level and the monitoring oxygen sensor. $VO_2$ is determined by detecting the amount of oxygen required to re-establish the preset oxygen level.

Although closed system, oxygen consumption monitoring has been realized for applications involving administration or monitoring of oxygen only, the advantages of developing such a system for concurrently applying anesthesia gas and oxygen suggest the greater utility of such a device. In such a system, all venting of dangerous gases is eliminated since the anesthesia gas remains confined to the closed system and patient. The closed system minimizes the amount of anesthesia and oxygen required and facilitates measurement of oxygen consumption and anesthesia uptake with simple and inexpensive feedback circuitry.

OBJECTIVES AND SUMMARY OF THE INVENTION

It is therefore an object of the present invention to provide a closed system oxygen monitoring device with instrumentation for concurrently introducing, monitoring and controlling anesthesia gas concentration level.

It is a further object of this invention to provide a general closed system anesthesia gas delivery system for automatically maintaining a preset level of anesthesia gas.

It is yet another object of this invention to provide means for monitoring and recording rates of oxygen consumption and anesthesia gas uptake for surgical patients.

This invention comprises a closed, recirculating delivery circuit for administering a preset volume of oxygen and anesthesia gas to a surgical patient. An oxygen sensor contained within the closed circuit monitors decreases in oxygen concentration within the recirculatory system and triggers restoration to the preset value by means of feedback comparator circuitry. The desired amount of anesthesia gas is preset and maintained by a potentiometric monitoring device operative in response to the peak expansion of a respirator bellows contained within the circuit. Variations from the preset level of anesthesia gas drive a servo-mechanism for replenishing

DETAILED DESCRIPTION OF THE DRAWING

Figure 1:
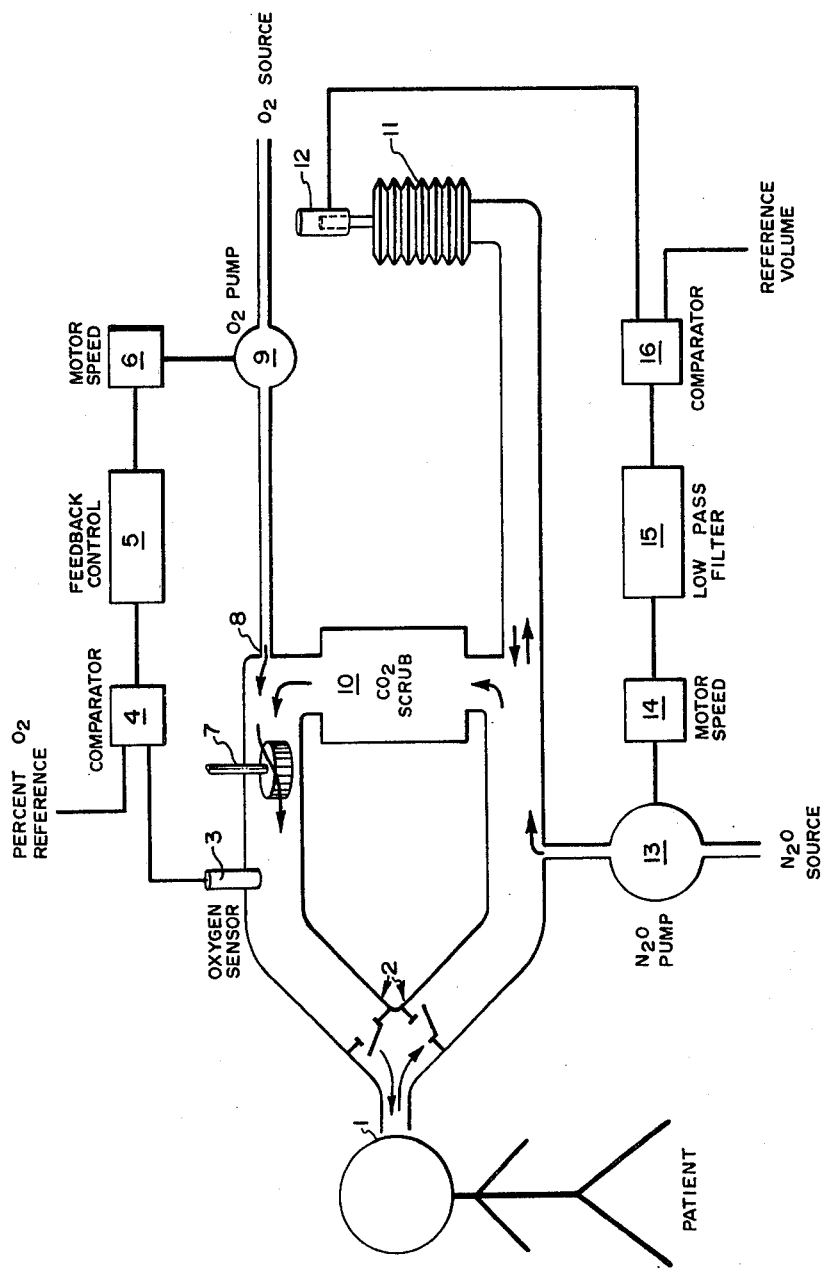

FIG. 1 shows a block diagram of the subject Oxygen and Anesthesia Delivery and Monitoring Device.

DETAILED DESCRIPTION OF THE INVENTION

Referring to FIG. 1, an oxygen-anesthesia consumption monitoring device is shown in which the patient is connected by an endotracheal tube, a mask, or a mouthpiece 1 to a closed rebreathing circuit. A pair of valves 2 forces the air to move counter-clock-wise around the loop. Carbon dioxide is removed from the exhaled air by a soda-lime carbon dioxide absorber 10 and oxygen is added by an oxygen pump 9 before the air returns to the patient. The respiratory bellows 11 provide forced ventilation when needed. An air circulator 7 in the circuit between the oxygen inlet port 8 and the oxygen sensor 3 serves to mix the gases before they reach the oxygen sensor.

A feedback control circuit is used to replace the oxygen that is consumed by the patient. A comparator circuit 4 detects any difference which exists between the preset reference oxygen concentration voltage and the oxygen sensor output. Any difference is applied to the input of an integrator and an amplifier 5, the outputs of which are summed to provide a voltage to the motor speed control circuit 6. The oxygen sensor acts as a null detector and the integrator and amplifier as first and second order elements in the feedback control loop.

Oxygen is pumped to the recirculating loop in response to the motor speed control circuit output until a null state is sensed between the oxygen sensor and reference voltage. By measuring the amount of oxygen introduced, an ongoing rate of oxygen consumption is provided.

The feedback loop which controls the nitrous oxide flow consists of a volume sensor, a feedback control circuit, and a nitrous oxide pump. The rebreathing circuit volume is monitored by a volume-variation sensitive means 12 which provides an output voltage proportional to peak volume experienced upon end expiration. A potentiometric sensor is shown in FIG. 1 and operates to register the peak volume expansion of the bellows 11 in the form of an output voltage. The feedback control circuit 16 compares this voltage with a reference voltage which is preset at an appropriate circuit volume. This difference is filtered through a low pass filter 15 and used to control the rate of nitrous oxide addition by the motor control 14 and pump 13 into the recirculation loop for maintaining a constant amount concentration of anesthesia.

This closed system replenishment technique offers several advantages. The measurement of the inspired or expired flow is not required eliminating the need for flow meters and associated instrumentation. The oxygen sensor serving as a null detector enables use of a simpler, less expensive sensor at higher inspired oxygen percents, thereby reducing costs and complexity. Since the inspired oxygen fraction is feedback-controlled and held constant, the constant attention of the anesthesiologist is not required and risks of human error are minimized. The uptake of anesthetic gases is automatically compensated for by means of servo-mechanisms which increase accuracy of anesthesia administration. Finally, the system can be applied to many respiratory system without major modifications.

We claim:

1. A closed, recirculating oxygen and anesthesia delivery circuit for monitoring and controlling rates of addition of oxygen and anesthesia gas in response to rates of oxygen consumption and anesthesia uptake, comprising:
   a. a closed circuit having at least one inlet means for addition of oxygen and at least one inlet means for addition of anesthesia gas to said circuit and outlet means for connecting said circuit to a patient, said system being operable to preserve a closed system environment between said circuit and the patient's lungs;
   b. first sensing means for detecting concentrations of oxygen within the closed circuit;
   c. flow controlling means for maintaining a single direction of gas flow across said oxygen concentration sensing means;
   d. first feedback means for comparing the detected oxygen concentration with a preset oxygen concentration indicator;
   e. first servo means including a motor-speed regulated pump responsive to said first feedback means and operable to maintain oxygen concentrations at a safe value relative to the preset oxygen concentration by regulating addition of oxygen through one or more of said oxygen inlet means, said motor-speed regulated pump being coupled at said oxygen inlet means for controlling oxygen feed into said closed circuit;
   f. second sensing means for detecting the concentration of the applied anesthesia gas within the closed system;
   g. second feedback means for comparing the detected anesthesia gas concentration with a preset anesthesia concentration indicator;
   h. second servo means including a motor-speed regulated pump responsive to said first feedback means and operable to maintain anesthesia concentrations at a safe value relative to the preset anesthesia concentration by regulating addition of anesthesia through one or more of said anesthesia inlet means, said motor-speed regulated pump being coupled at said anesthesia inlet means for controlling anesthesia feed into said closed circuit;
   i. means for reducing and maintaining $CO_2$ concentrations at safe levels within the closed system.

2. A closed, recirculating oxygen and anesthesia delivery circuit for monitoring and controlling rates of addition of oxygen and anesthesia gas in response to rates of oxygen consumption and anesthesia uptake, comprising:
   a. a closed circuit having at least inlet means for addition of oxygen and at least one inlet means for addition of anesthesia gas to said circuit and outlet means for connecting said circuit to a patient, said system being operable to preserve a closed system environment between said circuit and the patient's lungs;
   b. first sensing means for detecting concentrations of oxygen within the closed circuit;
   c. flow controlling means for maintaining a single direction of gas flow across said oxygen concentration sensing means;

d. first feedback means for comparing the detected oxygen concentration with a preset oxygen concentration indicator;
e. first servo means responsive to said first feedback means and operable to maintain oxygen concentrations at a safe value relative to the preset oxygen concentration by regulating addition of oxygen through one or more of said oxygen inlet means;
f. second sensing means for detecting the concentration of the applied anesthesia gas within the closed system;
g. second feedback means for comparing the detected anesthesia gas concentration with a preset anesthesia concentration indicator;
h. second servo means responsive to said second feedback means and operable to maintain anesthesia gas concentration by regulating addition of said anesthesia gas through one or more of said anesthesia inlet means;
i. circulating means spacially located between said oxygen inlet means and said first sensing means, said circulating means being operable to improve diffusion of replenished oxygen prior to contact therewith by said first sensing means; and
j. means for reducing and maintaining $CO_2$ concentration at safe levels within the closed sensor.

3. A closed, recirculating oxygen and anesthesia delivery circuit as defined in claim 2, wherein said second sensing means includes a bellows connected within said circuit, said bellows defining a volume which varies in response to variations in anesthesia gas concentration within said circuit and having a sensing means attached at said bellows for detecting peak volume variations thereof.

4. A closed, recirculating oxygen and anesthesia delivery circuit for monitoring and controlling rates of addition of oxygen and anesthesia gas in response to rates of oxygen consumption and anesthesia uptake, comprising:
a. a closed circuit having at least one inlet means for addition of oxygen and at least one inlet means for addition of anesthesia gas to said circuit and outlet means for connecting said circuit to a patient, said system being operable to preserve a closed system environment between said circuit and the patient's lungs;
b. first sensing means for detecting concentrations of oxygen within the closed circuit;
c. flow controlling means for maintaining a single direction of gas flow across said oxygen concentration sensing means;
d. first feedback means for comparing the detected oxygen concentration with a preset oxygen concentration indicator;
e. first servo means responsive to said first feedback means and operable to maintain oxygen concentrations at a safe value relative to the preset oxygen concentration by regulating addition of oxygen through one or more of said oxygen inlet means;
f. second sensing means comprising a bellows connected within said circuit, said bellows defining a volume which varies in response to variations in anesthesia gas concentration within said circuit and having a sensing means attached to said bellows for detecting peak volume variation thereof;
g. second feedback means coupled to the output of said second sensing means for comparing the detected anesthesia gas concentration with a preset reference concentration;
h. second servo means responsive to said second feedback means and operable to maintain anesthesia gas concentration by regulating addition of said anesthesia gas through one or more of said anesthesia inlet means; and
i. means for reducing and maintaining $CO_2$ concentration at safe levels within the closed system.

5. A closed, recirculating oxygen and anesthesia delivery circuit as defined in claim 4, wherein said sensing means attached at said bellows includes a potentiometric sensor which responds to changes in peak volume of said bellows with a corresponding change in voltage, thereby providing a signal to the second feedback means representing circuit volume changes.

6. A closed, recirculating oxygen and anesthesia delivery circuit as defined in claim 1, wherein said second sensing means includes a bellows connected within said circuit, said bellows defining a volume which varies in response to variations in anesthesia gas concentration within said circuit and having a sensing means attached at said bellows for detecting peak volume variations thereof.

7. A closed, recirculating oxygen and anesthesia delivery circuit as defined in claim 6, wherein said sensing means attached at said bellows includes a potentiometric sensor which responds to changes in peak volume of said bellows with corresponding change in voltage, thereby providing a signal to the second feedback means representing circuit volume changes.

* * * * *